(12) United States Patent
Monstadt (10) Patent No.: US 8,480,701 B2
(45) Date of Patent: Jul. 9, 2013

(54) DEVICE FOR IMPLANTING ELECTRICALLY ISOLATED OCCLUSION HELIXES

(75) Inventor: Hermann Monstadt, Bochum (DE)

(73) Assignee: Dendron GmbH (DE)

( * ) Notice: Subject to any disclaimer, the term of this patent is extended or adjusted under 35 U.S.C. 154(b) by 590 days.

(21) Appl. No.: 10/597,299

(22) PCT Filed: Jan. 21, 2005

(86) PCT No.: PCT/EP2005/000587
§ 371 (c)(1),
(2), (4) Date: Aug. 12, 2008

(87) PCT Pub. No.: WO2005/070308
PCT Pub. Date: Aug. 4, 2005

(65) Prior Publication Data
US 2010/0076479 A1    Mar. 25, 2010

(30) Foreign Application Priority Data

Jan. 21, 2004 (DE) .......................... 10 2004 003 265

(51) Int. Cl.
*A61B 18/04* (2006.01)
*A61B 17/08* (2006.01)
*A61F 11/00* (2006.01)
*A61M 29/00* (2006.01)
*A61D 1/00* (2006.01)

(52) U.S. Cl.
USPC .............. 606/200; 606/32; 606/108; 606/213

(58) Field of Classification Search
USPC .......................................... 606/194, 200, 213
See application file for complete search history.

(56) References Cited

U.S. PATENT DOCUMENTS

| 5,122,136 A | 6/1992 | Guglielmi et al. |
| 5,354,295 A | 10/1994 | Guglielmi et al. |
| 5,423,829 A | 6/1995 | Pham et al. |

(Continued)

FOREIGN PATENT DOCUMENTS

| DE | 101 18 017 A1 | 10/2002 |
| EP | 484468 | 6/1999 |

OTHER PUBLICATIONS

Co-pending U.S. Appl. No. 13/010,671, filed Jan. 20, 2011.

*Primary Examiner* — Gary Jackson
*Assistant Examiner* — Michael Mendoza
(74) *Attorney, Agent, or Firm* — Elizabeth A. O'Brien (57) ABSTRACT

The invention relates to a device for the implantation of occlusion helixes (3) that can be separated by electrolysis in blood vessels and body cavities, especially aneurysms (12), said device comprising an insertion aid (4), at least one occlusion helix (3) that is distally arranged in relation to the insertion aid (4) and at least one electrolytically corrodible severance element (2), with at least one stabilization helix (5) being arranged between severance element (2) and occlusion helix (3) and said stabilization helix (5) being connected with the occlusion helix (3) by an electrically isolating adhesion layer (7) such that the occlusion helix (3) becomes isolated from the voltage when an electrical voltage is applied to the severance element (2). In this way, the current density in severance element (2) is further increased so that, on the one hand, shorter severance times are achieved and, on the other, the connection between the occlusion helix (3) and one of the stabilization helixes (5) used to stabilize the implant is significantly simplified compared to the known laser welding method according to prior art.

30 Claims, 3 Drawing Sheets

U.S. PATENT DOCUMENTS

| Patent No. | | Date | Inventor(s) |
|---|---|---|---|
| 5,540,680 | A | 7/1996 | Guglielmi et al. |
| 5,624,449 | A | 4/1997 | Pham et al. |
| 5,658,308 | A | 8/1997 | Snyder |
| 5,690,667 | A | 11/1997 | Gia |
| 5,851,206 | A | 12/1998 | Guglielmi et al. |
| 5,853,418 | A | 12/1998 | Ken et al. |
| 5,855,578 | A | 1/1999 | Guglielmi et al. |
| 5,891,128 | A | 4/1999 | Gia et al. |
| 5,895,385 | A | 4/1999 | Guglielmi et al. |
| 5,919,187 | A | 7/1999 | Guglielmi et al. |
| 5,925,037 | A | 7/1999 | Guglielmi et al. |
| 5,928,226 | A | 7/1999 | Guglielmi et al. |
| 5,935,145 | A | 8/1999 | Villar et al. |
| 5,941,888 | A | 8/1999 | Wallace et al. |
| 5,944,714 | A | 8/1999 | Guglielmi et al. |
| 5,947,962 | A | 9/1999 | Guglielmi et al. |
| 5,947,963 | A | 9/1999 | Guglielmi |
| 5,976,126 | A | 11/1999 | Guglielmi et al. |
| 5,984,929 | A | 11/1999 | Bashiri et al. |
| 6,010,498 | A | 1/2000 | Guglielmi |
| 6,013,084 | A | 1/2000 | Ken et al. |
| 6,066,133 | A | 5/2000 | Guglielmi et al. |
| 6,077,260 | A | 6/2000 | Wheelock et al. |
| 6,083,220 | A | 7/2000 | Guglielmi |
| 6,123,714 | A | 9/2000 | Gia et al. |
| 6,146,373 | A | 11/2000 | Cragg et al. |
| 6,156,061 | A | 12/2000 | Wallace et al. |
| 6,165,178 | A | 12/2000 | Bashiri et al. |
| 6,280,457 | B1 | 8/2001 | Wallace |
| 6,371,972 | B1 | 4/2002 | Wallace et al. |
| 6,425,893 | B1 | 7/2002 | Guglielmi |
| 6,468,266 | B1 | 10/2002 | Bashiri et al. |
| 6,485,524 | B2 | 11/2002 | Strecker |
| 6,511,468 | B1 | 1/2003 | Cragg et al. |
| 6,558,367 | B1 | 5/2003 | Cragg et al. |
| 6,620,152 | B2 | 9/2003 | Guglielmi |
| 6,964,657 | B2 | 11/2005 | Cragg et al. |
| 7,166,122 | B2 * | 1/2007 | Aganon et al. ................ 606/200 |
| 7,238,194 | B2 | 7/2007 | Monstadt et al. |
| 7,300,458 | B2 | 11/2007 | Henkes et al. |
| 7,323,000 | B2 * | 1/2008 | Monstdt et al. ............... 606/200 |
| 7,524,322 | B2 | 4/2009 | Monstdt et al. |
| RE41,029 | E | 12/2009 | Guglielmi et al. |
| 7,879,064 | B2 | 2/2011 | Monstadt et al. |
| 7,896,899 | B2 | 3/2011 | Patterson et al. |
| 2002/0151883 | A1 | 10/2002 | Guglielmi |
| 2003/0014073 | A1 | 1/2003 | Bashiri et al. |
| 2003/0040733 | A1 | 2/2003 | Cragg et al. |
| 2003/0225365 | A1 | 12/2003 | Greff et al. |
| 2005/0079196 | A1 | 4/2005 | Henkes et al. |
| 2006/0036281 | A1 | 2/2006 | Patterson et al. |
| 2008/0045922 | A1 | 2/2008 | Cragg et al. |
| 2008/0051803 | A1 | 2/2008 | Monjtadt et al. |
| 2008/0103585 | A1 | 5/2008 | Monstadt et al. |
| 2008/0125855 | A1 | 5/2008 | Henkes et al. |
| 2008/0228215 | A1 | 9/2008 | Strauss et al. |
| 2008/0228216 | A1 | 9/2008 | Strauss et al. |
| 2008/0319532 | A1 | 12/2008 | Monstadt et al. |
| 2009/0254111 | A1 | 10/2009 | Monstadt et al. |
| 2010/0023105 | A1 | 1/2010 | Levy et al. |
| 2010/0030200 | A1 | 2/2010 | Strauss et al. |
| 2010/0049165 | A1 | 2/2010 | Sutherland et al. |
| 2011/0098814 | A1 | 4/2011 | Monstadt et al. |

* cited by examiner

DEVICE FOR IMPLANTING ELECTRICALLY ISOLATED OCCLUSION HELIXES

The invention relates to a device for implanting occlusion helixes that can be detached by electrolysis in blood vessels and body cavities, especially aneurysms, said device comprising an insertion aid, at least one occlusion helix that is distally arranged in relation to the insertion aid and at least one electrolytically corrodible severance element, with at least one stabilization helix being arranged between severance element and occlusion helix.

The use of endovascular techniques for the occlusion of body cavities or vessels such as arteries, veins, fallopian tubes or vascular deformities (for example, vascular aneurysms) is known in the art. In this case, the occlusion helix is usually introduced by means of an endovascular guide wire serving as insertion aid through a catheter into the cavity to be occluded and deposited therein.

To detach the occlusion helix from the insertion aid various methods are known from prior art. In particular, the electrolytic severance of stainless steel wire ends as initially described for electro-coagulation by Thompson et al. as well as McAlister et al. in 1979 has proved its worth in this context (Radiology 133:335-340, November 1979; AJR 132:998-1000, June 1979).

Based on this method European patent publication 0 484 468 as well describes a device for the implantation of occlusion helixes involving the electrolytically corrodible design of the end of the guide wire at the connection between the guide wire and the occlusion helix. In this manner the electrical voltage applied to the occlusion helix serving as an anode for electro-thrombozation is utilized for the simultaneous severance of the wire end and thus the release of the occlusion helix.

All devices of this nature have the disadvantage in that the guide wire intended for the safe transfer of the implant has to be of comparatively massive design which means severance of the guide wire end by means of electrolysis requires a relatively long period of time. For this reason, WO 03/017852 A1 proposes to design an electrolytically corrodible point in the form of a severance element as part of the occlusion helix proper. Since these severance elements are subjected to significantly lower bending stresses during the implantation process they may have a correspondingly smaller diameter resulting in the electrolytic detachment of the occlusion helix to improve and be carried out more quickly. It has, moreover, been possible in this way to use less stable and more flexible materials for the severance element which additionally accelerated and improved the detachment process by means of electrolysis.

Furthermore, the application of stabilization helixes is known from prior art said helixes serve the purpose of connecting the severance elements with the occlusion helixes. These stabilization elements are intended to stabilize and stiffen the implant and are of a diameter that is smaller than that of the occlusion helixes so that they can be inserted at least partly into the latter. Moreover, the stabilization helixes connected to the severance elements also serve to enlarge the surface at the end of the severance element in order to improve in this manner the connectability with respect to the occlusion helix. The connection is as a rule established with the help of a laser welding process, however connecting a severance element without stabilization helix to the occlusion helix would turn out to be rather difficult due to the small diameter of the severance element. Although the connection could thus be more easily established as a result of the additionally attached stabilization helix bringing about a correspondingly larger surface, laser welding nevertheless is a very complex and sophisticated technology to be applied so that there is need for a more simple technique enabling the stabilization and occlusion helixes to be connected.

To keep the severance times to a minimum it has been disclosed by prior art publications, for instance U.S. Pat. No. 6,620,152, that the implant be isolated electrically which apparently increases the disposition of the wire section envisaged for electrolytic severance to be more vulnerable to electrolytic corrosion. Isolation in this case may be brought about either by arranging isolation between the implant and the severance location or by coating the implant with an isolating layer.

However, this prior-art technique has the disadvantage in that the severance location of the device described in the cited publication is situated in the guide wire which compared to arranging the severance location in the area of the occlusion helix is less beneficial for the reasons stated above and described in sufficient detail in WO 03/017852 A1 to which express reference is made here.

Furthermore, no additional stabilization helixes which serve to position and improve the transition to the occlusion helix have been provided for the isolated implants known from prior art as referred to above.

Proceeding from what is known from prior-art it is therefore the objective of the invention to provide a device for the implantation of occlusion helixes which enables the time span required for electrolytic corrosion to be further reduced and, what is more, provides also for a simplified connection between stabilization helix and occlusion helix.

According to the invention this objective is achieved by providing a device for the implantation of occlusion helixes that can be detached by electrolysis in blood vessels and body cavities, especially aneurysms, said device comprising an insertion aid, at least one occlusion helix that is distally arranged in relation to the insertion aid and at least one electrolytically corrodible severance element, with at least one stabilization helix being arranged between severance element and occlusion helix and said stabilization helix being connected with the occlusion helix by an electrically isolating adhesion layer such that the occlusion helix becomes isolated from the voltage when an electrical voltage is applied to the severance element.

Other than the isolations known from prior art the isolation proposed by the invention is not located between severance location and implant but between the individual components of the implant. In this manner two problems are resolved simultaneously, that is simplifying the connection of stabilization and occlusion helix on the one hand and shortening the severance time on the other. The latter is due to the fact that when voltage is applied to the severance element the current density in said element increases provided other parts of the implant where electrolytic corrosion shall not take place are isolated from the voltage so applied.

At the same time, establishing the connection between stabilization and occlusion helix is significantly simplified in comparison to prior-art solutions usually proposing the use of laser welding techniques. As proposed by the invention the usual course of action calls for an adhesive being applied to at least that end of the stabilization helix that is envisaged to be connected to the occlusion helix with said stabilization helix then being brought in contact with the occlusion helix. It is to be considered especially advantageous to provide the entire stabilization helix with an electrically isolating coating said coating may, in particular, consist of an adhesive layer. Following this, one end of the stabilization helix can be brought into contact with the occlusion helix or partly inserted into the same to establish a durable, isolating connection. As a result of the additional isolation of the stabilization helixes by means of an electrically isolating coating any corrosion in the area of the stabilization helix is prevented and the current density in the area of the severance element increased further which leads to the severance time being reduced correspondingly. If thought expedient, even several stabilization helixes fit together may be arranged at the occlusion helix.

It is, moreover, considered expedient to arrange for a securing means to be run through the lumen of the occlusion helix. Securing means of this nature offer the advantage that in the event of a wrong placement of the occlusion helix or if too large an occlusion helix has been selected for the area to be occluded and must then be retracted, possibly completely retracted into the catheter such retraction process is much safer. Retracting an occlusion helix without securing means involves a risk in that portions of the helix are pulled apart and elongated due to the tensile or torsional stresses applied and in this way be plastically deformed irreversibly. In extreme cases the helix may separate or break giving rise to life-threatening embolism.

It is known to provide for such securing means to consist of flexible polymer threads. However, especially preferred is a variant that is described in DE 101 18 017 A1 according to which the securing means consist of a wire made of a material, particularly a metal, having shape memory properties. In comparison with securing elements made of a polymer material such a metallic securing means offers distinct advantages with respect to its resistance to torsional or tensile stresses. A securing means made of a metal having shape memory properties may also offer characteristics known as "super elasticity" so that such a securing means or element in its flexible state can withstand particularly high bending or tension loads without the risk of failing or breaking.

As regards the shape-memory properties of the securing means these may be due to a thermal or mechanical shape-memory effect. Especially proven materials used for this purpose are titanium and nickel containing alloys, in particular an alloy known to those skilled in the art under the name of Nitinol. Furthermore, alternative materials may be used as well, for example iron or copper based alloys. The properties of the shape-memory material can be precisely controlled or influenced by a person skilled in the art in a known manner by selecting exactly the material composition required. The diameter of such a wire serving as securing means typically ranges between 0.03 and 0.05 mm.

Moreover, using a shape-memory material for the securing means is also conducive to the impression of a superimposed structure on the occlusion helix after said helix has been released from the catheter and placed in an aneurysm, for example. It is, basically, of advantage if the occlusion helix forms into such a secondary structure when in the aneurysm, for instance takes on helical coil or basket shape, because in this way the aneurysm is filled up particularly well to make sure an effective thrombozation of the aneurysm can be achieved. If thought expedient the occlusion helix itself may be preformed into such a superimposed structure which it assumes when it is released from the catheter. It may nevertheless be sufficient, however, if exclusively the securing means and not the occlusion helix itself is preformed, provided the force exerted by the securing means is great enough to also force the occlusion helix into the shape predetermined by the securing means. The force exerted by the securing means is brought about due to the securing means being liberated and released from the constraint of the surrounding catheter when placed into the aneurysm and re-transformed returning to its austenite phase which causes it to assume the previously impressed structure. Additionally or alternatively, a temperature induced transformation may be caused as well when, upon being released from the catheter, the securing means is subjected to the elevated temperature prevailing in the blood stream.

If only one severance element is provided or in the event of several severance elements in the area of the most distally arranged segments of the occlusion helix the securing means is expediently arranged between stabilization helix and distal front section of the occlusion helix, i.e. at its proximal end it is attached to the stabilization helix and at its distal end to the occlusion helix. To make sure an electrical connection between stabilization helix and occlusion helix is not established via the securing means the connection of the securing means to the distal front section of the occlusion helix is suitably effected with the aid of an adhesion layer which enables the occlusion helix to be isolated from an electrical voltage applied to the severance element. The connection between stabilization helix and metallic securing means may also be made up by means of an adhesion layer or by welding or soldering methods to suit individual needs. In case an adhesion layer is used the securing means as well is electrically isolated from the severance element whereas the voltage applied to the severance element for the purpose of electrolytic corrosion is also applied to the securing means in case welding or soldering techniques are employed. As described in more detail hereinafter the latter may be beneficial in certain cases.

In order to prevent in the latter case that a current flow occurs when contact is made between the metallic securing means and the occlusion helix the securing means should be provided with an electrically isolating coating similar to the one that can be used for the stabilization helix. Such a coating is all the more useful because it prevents the electrolytic corrosion of the securing means proper and keeps the current density at the severance element at a high level.

As an alternative to the electrical isolation of the securing means the occlusion helix itself may be provided with an electrically isolating coating, at least on the inside of the helix. In this manner as well it is effectively ruled out that a current flow occurs between securing means and occlusion helix as soon as both elements contact each other.

Especially preferred are devices according to which the occlusion helix is provided with several spaced electrolytically corrodible severance elements or devices with several spaced occlusion helixes provided with one electrolytically corrodible severance element each arranged between them. Devices of this type are basically known from WO 01/32085 A1 to which express reference is made here. In this manner one or several variably sized longitudinal sections of the occlusion helix can be separated by electrolysis and placed in the aneurysm. This enables occlusion helixes of exactly the right length to be placed into the aneurysm. If necessary, even several sections of the same helix may be separated one after the other and introduced into the cavity to be occluded. This is beneficial not only in terms of costs and time but also serves to further minimize surgery risks. Furthermore, the application of this method dispenses with the need to always keep ready and use differently sized occlusion helixes for placement into aneurysms of different size but instead enables a uniformly sized device to be employed which makes it possible, as required in each individual case, to introduce differently sized sections of the occlusion helix into the aneurysm.

The application of such occlusion helixes having a plurality of electrolytically corrodible locations is based on findings according to which the specific severance location of the occlusion helix that is situated nearest to the distal end of the catheter is separated by electrolysis when a current is applied to such a device. This is due to the fact that on the one hand the electrolytically corrodible locations in the catheter are isolated from the ionic medium through the catheter and thus are not undergoing electrolysis and, on the other hand, the current density decreases in proximal-distal direction owing to the distally increasing resistance in the occlusion helix or helixes. As a result of this, the electrolytically corrodible point which, viewed in distal direction, is closest to the distal end of the catheter is subjected to the most intensive electrolytic process and is thus preferentially dissolved.

In the event of a device having a plurality of severance elements it is expedient to arrange in the segments of the occlusion helix located between the severance elements or in the individual occlusion helixes one securing means each which passes through the lumen of the occlusion helix. In this manner the placement of variably sizable lengths is at the same time associated with securing each individual segment arranged between the electrolytically corrodible points such that a maximum degree of safety is achieved with respect to preventing the occlusion helixes from being torn off.

According to an especially preferred embodiment the individual severance elements are connected in an electrically conductive fashion via metallic securing means. As per the aforesaid embodiment the securing means, although isolated with respect to the occlusion helix, passes the current on to the next, distally arranged severance element. The transition in this case may be effected such that the securing means is directly connected with the nearest severance element or in such a way that the securing means has a conductive connection with an additional stabilization helix at the distal end of a segment of an occlusion helix or with one of several occlusion helixes arranged in series, again with the stabilization helix being conductively connected with the severance element. Typically, on both ends of the severance elements a stabilization helix each is arranged said helix connecting the severance element with the respective occlusion helix segments. Preferably, each individual securing means runs from the stabilization helix located on the distal end of a severance element to the nearest distally located stabilization helix of the following severance element. In this manner it is ensured that the individual severance elements are connected in an electrically conductive manner via the stabilization helixes and the securing means attached to said helixes such that an applied electrical voltage intended to separate the occlusion helixes is transferred to the individual severance elements. At the same time each individual occlusion helix segment is isolated electrically from the stabilization helix because said segment being attached to the stabilization helix with the aid of an electrically isolating adhesion layer. Basically, the metallic securing means may also be secured to the severance elements proper and in this manner make sure the flow of current is established. Only with the most distally arranged occlusion helix segment does the securing means preferably run up to the distal front section of the occlusion helix proper where the securing means is connected with the distal front section via an adhesion layer isolating the occlusion helix from the electrical voltage applied with a view to bringing about electrolytic corrosion.

In addition, the securing means is preferably provided with an electrically isolating coating so that electric current in fact flows in distal direction through the interior of the securing means but neither an electrolytic corrosion nor electrical contact with the occlusion helix will occur in this area. As a result of the measures described above a very elegant method is provided for the creation of variably separable occlusion helixes and, moreover, also the current density at the severance element is kept particularly low leading to the severance times being correspondingly reduced. Furthermore, this embodiment offers manufacturing advantageous as a connection brought about by adhesion layers is easier made up than by means of the laser welding techniques known from prior art.

For the build-up of the adhesion layers and electrically isolating coatings on the securing means and/or stabilization helixes a variety of materials are considered suitable on principle. An important factor to be observed in this context is naturally the compatibility with and, evenly significant, the approval for medical applications.

Aside from bio-compatibility and isolating properties the hardenability of the adhesive is also of advantage, with adhesives that can be hardened by radiation, e.g. UV-hardenable adhesives, offering particular benefits because the radiation introduced to harden the material will, as the case may be, have also a sterilizing effect. The use of acrylate adhesives is considered to be particularly expedient although, basically, other adhesives having the aforesaid characteristics are similarly suitable.

Especially preferred is the use of a material commercially available under the tradename of "Permabond", said material being approved and having excellently proved its worth in the medical field. Permabond 4L25 marketed by National Starche & Chemical Company (ICI) is a UV-hardenable adhesive suitably employed in the medical sector for the connection of a variety of substances. Said material is an adhesive on acrylate basis that can be hardened at wavelengths ranging between 320 and 380 nm. After hardening Permabond passes USP class VI tests. Permabond is also insensitive to gamma radiation and a number of other sterilization processes.

The severance elements designed to be quickly corrodible preferably consist of alloyed steel. In this connection, the stainless steel grades of type AISI 301, 303 or 316 and/or subgroups of these types are particularly preferred. Stainless steel material of this type preferably has a chromium content of between 12 and 20% w/w. Examples in this case are steel grades 1.4410, 1.4310, 1.4301 and 1.4122. Suitable, for example, are chromium-nickel steels of grade 18/8. The diameter of the severance elements typically ranges between 0.01 and 0.05 mm.

To shorten the severance times even more the severance elements may be pre-corroded. Such a pre-corrosion may, for example, be achieved by heat treatment which causes the metal structure to be modified such that it very quickly disintegrates in an electrolyte when an electric voltage is applied. The heat treatment required for this can be carried out with the help of a laser, in a customary furnace or by means of an induction coil. The temperature range required for this is approximately 500 to 1000° C., preferably 600 to 950° C. and in particular 700 to 900° C. It is assumed that such a heat treatment causes recrystallization accompanied by the formation of large microstructural grains and hard metal carbides which results in the grain boundary stability to diminish. The formation of chromium carbides segregating at the grain boundaries leads to a chromium depletion of the matrix and furthermore brings down the resistance to intergranular corrosion. This will quickly enlarge the surface available for corrosion so that the structure will rapidly decompose within an electrolyte when a current has been applied.

Another possibility to design the severance elements so as to be well corrodible is to make use of material combinations for the relevant areas that are conducive to the formation of local elements. Examples in this case are combinations of stainless steels with noble metals or noble metal alloys, in particular platinum alloys.

The occlusion helixes proper are expediently made of platinum or platinum alloys which have proven their worth. Especially preferred here is the use of platinum-iridium alloys. The stabilization helixes connected to the severance elements usually consist of alloyed steel material, like the one used for the severance elements themselves, however, a platinum alloy similar to that employed for the occlusion helixes may basically also be used for the stabilization helixes. Using an alloyed steel material offers certain benefits in that the radiopacity between severance element and stabilization helix, on the one hand, and occlusion helix on the other increases. This is due to the fact that platinum alloys have a radiopaqueness that is by far higher than that of steel alloys.

The insertion aid is preferably a customary guide wire of proven design for the purpose of passing occlusion helixes through a catheter towards a cavity to be occluded.

The device according to the invention may also be directly combined with a micro-catheter by means of which the occlusion helix is brought to the placement site. The catheter used and the employed occlusion helix in this case shall be matched with respect to their size. If necessary, the catheter also may exert constraint on the occlusion helix as well as securing means resulting in the occlusion helix to assume in the aneurysm its or the securing means' previously impressed secondary structure not earlier than after it has been liberated and released from such constraint. Expediently, the catheter is moreover provided with radiopaque markers enabling a placement in the target area with the aid of known imaging methods.

Aside from the device for the implantation of electrolytically severable occlusion helixes the invention furthermore relates to a corresponding medical implant comprising at least one occlusion helix, at least one severance element and at least one stabilization helix, with the stabilization helix being arranged between severance element and occlusion helix so that the severance element and occlusion helix are indirectly connected in this manner, and with the stabilization helix being attached to the occlusion helix by means of an electrically isolating adhesion layer.

Further elucidation of the invention is provided by way of examples through the enclosed figures, where.

Figure 1:
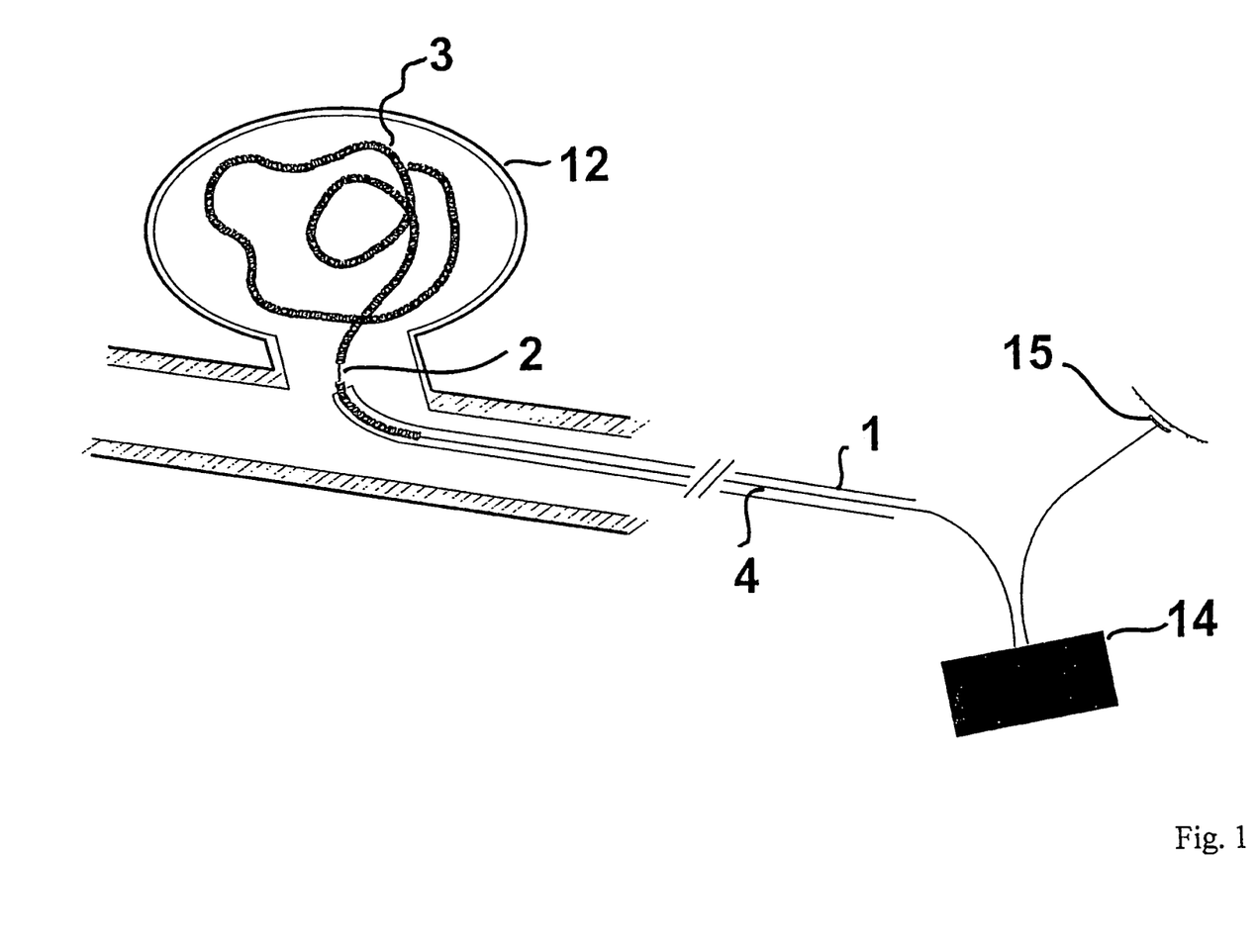
FIG. 1 is a schematic representation showing the positioning of an occlusion helix in an aciniform aneurysm with the help of the inventive device.

FIG. 1 shows a vertical view of the occlusion helix 3 placed into an aciniform aneurysm 12. The occlusion helix 3 is moved distally within catheter 1 with the help of the guide wire 4. When correctly positioned the occlusion helix 3 exits from the end of catheter 1 and is introduced into and fills up the cavity formed through the aciniform aneurysm 12. Within the aneurysm 12 the occlusion helix 3 forms secondary coils or turns which in particular can be caused by a stress- and/or temperature-induced transformation from its martensitic to its austenitic phase of the occlusion helix 3 and/or securing means, which has not been shown here, inside the occlusion helix 3. Due to the formation of secondary coils or turns the aneurysm 12 is filled up particularly effectively.

As soon as a certain length of the occlusion helix 3, which suits the volume of the cavity to be filled, has been placed into the aneurysm 12 the electrolytic separation is effected at the severance element 2. For this purpose, an electric voltage coming from voltage source 14 is applied to severance element 2 with the severance element 2 serving as anode. The cathode 15 is positioned on the body surface. With the device according to the invention the electrolytic corrosion of severance element 2 occurs particularly quickly, within time spans usually well below 1 min., i.e. within approx. 20 to 40 s (at 2 V, 2 mA). As per a preferred embodiment several severance elements 2 are provided within the area of the occlusion helix 3 so that the length of the occlusion helix 3 introduced can be appropriately sized to suit the respective aneurysm 12.

Figure 2:
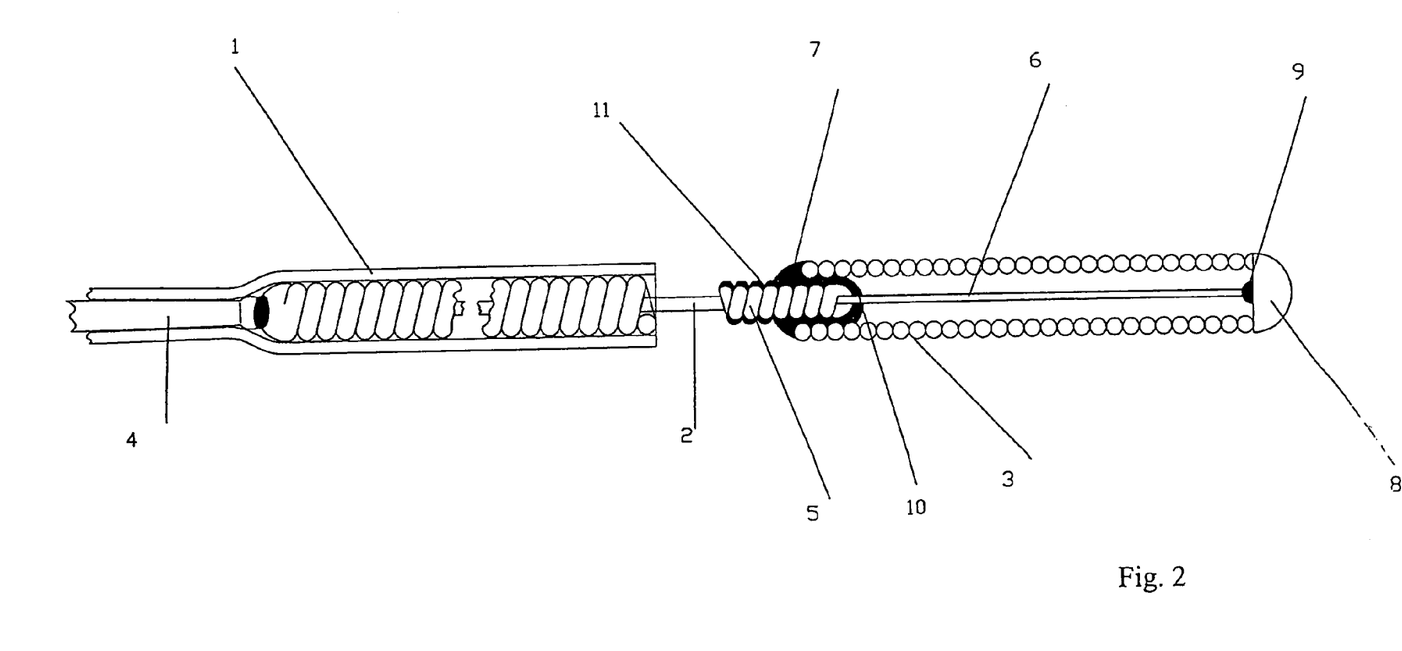
FIG. 2 is a longitudinal section through the inventive device which in comparison to FIG. 1 is of significantly enlarged representation.

In FIG. 2 the device according to the invention is shown schematically as a longitudinal section. The occlusion helix 3 shown in this figure is attached to severance element 2 by means of stabilization helix 5, said latter stabilization helix 5 being of smaller diameter than the occlusion helix 3 with the outside diameter of the stabilization helix 5 basically coinciding with the inside diameter of the occlusion helix 3. Accordingly, the stabilization helix 5 can be inserted, at least partially, into the occlusion helix 3.

Stabilization helix 5 and occlusion helix 3 are interconnected via an adhesion layer 7, said adhesion layer 7 simultaneously isolating the occlusion helix 3 from the electric voltage applied to the severance element 2. In this manner, the current density in severance element 2 is kept at a particularly high level. An additional coating 11 applied to stabilization helix 5 serves to intensify this effect even more. The current applied with a view to separating the occlusion helix 3 can be passed on to the severance element 2 via guide wire 4.

Additionally, a securing means 6 is arranged in the lumen of the occlusion helix 3, said means being a Nitinol wire which is provided with an isolating coating or layer. This securing means 6 extends from the stabilization helix 5 to the distal end 8 of occlusion helix 3. At this point the securing means 6 is connected to the distal end 8 of occlusion helix 3 with the aid of another isolating adhesive layer 9. Permabond is used for producing the adhesive layers 7 and 8 as well as the coating of the stabilization helix 5.

For the purpose of producing the inventive device a stabilization helix 5 is initially provided with a Permabond layer or coating following which the securing means 6 designed as a Nitinol wire is welded to the stabilization helix 5 at location 10, i.e. at the distal end of stabilization helix 5. Finally, the stabilization helix 5 is attached to the occlusion helix 3 by means of Permabond.

Figure 3:
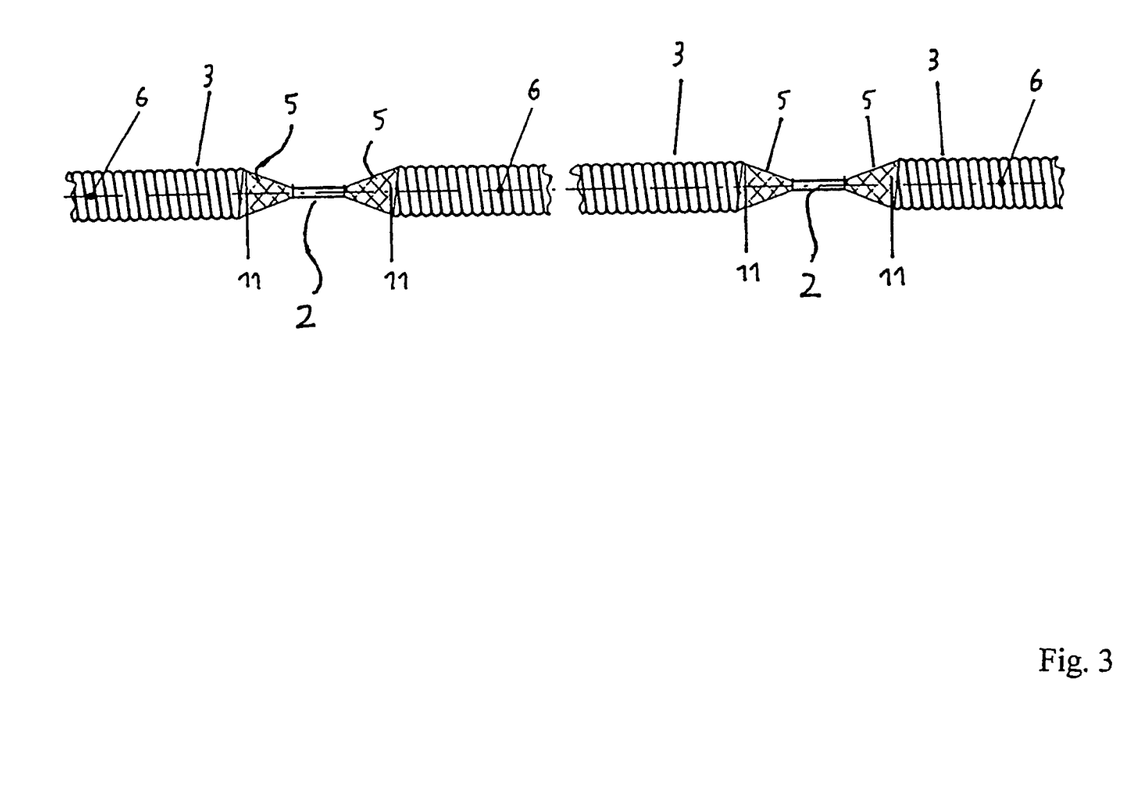
FIG. 3 is a longitudinal section of the inventive device showing several severance elements.

FIG. 3 shows a device according to the invention having a plurality of severance elements 2. The device has been provided with a plurality of occlusion helix segments 3 so that separation can be effected as desired at different severance elements 2 to suit the size of the aneurysm to be occluded. In this case, each severance element 2 is connected with the respective occlusion helix segment 3 via a stabilization helix 5 with such connection being made up according to the invention through the provision of an electrically isolating adhesion layer. In addition, the stabilization helix 5 in this case is provided with coating 11 that also has electrically isolating characteristics.

Through the lumen of the relevant occlusion helix segments 3 extends a metallic securing means 6 which is provided with an electrically isolating coating to safely isolate the securing means 6 from the occlusion helix 3. However, through the interior of securing means 6 an electric current is passed on in distal direction to the relevant severance element 2 where the electrolytic corrosion can be initiated as desired and when necessary. Within an occlusion helix segment 3 the metallic securing means 6 extends in each case from the stabilization helix 5 which is proximally attached to the occlusion helix segment 3 to the stabilization helix 5 distally connected to the occlusion helix segment 3. In this way, the electric current is passed from one severance element 2 via stabilization helix 5 attached to it, the securing means 6 in distal direction to the subsequent stabilization helix 5 and on to the severance element 2 connected with it. Accordingly, securing means 6 is advantageously utilized in that it not only provides increased safety in the event the occlusion helix 3 is wrongly placed but moreover serves to establish an electrically conductive connection of the individual severance elements 2.

The invention claimed is:

1. A device for the implantation of occlusion helixes that can be separated by electrolysis in blood vessels and body cavities, such as aneurysms, said device comprising:
   an insertion aid;
   at least one occlusion helix that is distally arranged in relation to the insertion aid, the at least one occlusion helix comprising a longitudinally-oriented lumen;
   a securing means extending through the lumen to a distal front section of the at least one occlusion helix; and
   at least one electrolytically corrodible severance element, with at least one stabilization helix being arranged between the at least one electrolytically corrodible severance element and the at least one occlusion helix,
   the securing means being in electrical communication with the at least one electrolytically corrodible severance element and the at least one stabilization helix;
   said stabilization helix being connected to the at least one occlusion helix with an electrically isolating adhesion layer such that the at least one occlusion helix is electrically isolated, by the adhesion layer, from the at least one electrolytically corrodible severance element and the at least one stabilization helix,
   wherein said at least one securing means is connected to the distal front section of the at least one occlusion helix with a distal electrically isolating adhesion layer;
   wherein a helical distal portion of the at least one stabilization helix axially overlaps at least a portion of the at least one occlusion helix, and a helical proximal portion of the at least one stabilization helix does not axially overlap the at least one occlusion helix.

2. The device according to claim 1, wherein the stabilization helix comprises an electrically isolating coating.

3. The device according to claim 2 wherein the electrically isolating coating comprises an acrylate adhesive.

4. The device according to claim 1, wherein the securing means extends longitudinally through the lumen of the occlusion helix.

5. The device according to claim 1, wherein the securing means comprises a material having shape-memory properties.

6. The device according to claim 5, wherein the securing means is configured to transform and assume a previously impressed structure configuration when placed into the blood vessel or body cavity.

7. The device according to claim 1, wherein the securing means comprises Nitinol.

8. The device according to claim 1, wherein at least one securing means extends from the stabilization helix to the distal front section of the at least one occlusion helix.

9. The device according to claim 8, wherein the electrically isolating distal adhesion layer is configured to isolate the occlusion helix from an electrical voltage applied to the severance element.

10. The device according to claim 1, wherein the securing means is provided with an electrically isolating coating.

11. The device according to claim 1, wherein the at least one occlusion helix comprises an inner side with an electrically isolating coating.

12. The device according to claim 1, wherein the at least one occlusion helix is provided with a plurality of spaced electrolytically corrodible severance elements.

13. The device according to claim 1, further comprising a plurality of spaced occlusion helixes with an electrolytically corrodible severance element arranged between pairs of the individual spaced occlusion helixes.

14. The device according to claim 12, further comprising a securing means arranged in a segment of the at least one occlusion helix located between the plurality of spaced electrolytically corrodible severance elements.

15. The device according to claim 14, wherein at least one of the securing means extends from one stabilization helix connected by a severance element to the next distally located stabilization helix.

16. The device according to claim 14, wherein at least one of the securing means extends from one severance element to the next distally located severance element.

17. The device according to claim 12, wherein the plurality of spaced electrolytically corrodible severance elements are connected with each other so as to be electrically conductive via the securing means extending through the lumen of the at least one occlusion helix.

18. The device according to claim 12, wherein the plurality of spaced severance elements have an electrically conductive connection with each other.

19. The device according to claim 1, wherein the electrically isolating adhesion layer comprises an acrylate adhesive.

20. The device according to claim 1, wherein the at least one electrolytically corrodible severance element comprises a steel alloy material.

21. The device according to claim 1, wherein the at least one electrolytically corrodible severance element is pre-corroded.

22. The device according to claim 1, wherein the occlusion helixes comprise the material selected from the group consisting of platinum a platinum alloy, and a platinum-iridium alloy.

23. The device according to claim 1, wherein the insertion aid is a guide wire.

24. The device according to claim 1, wherein said device is a micro-catheter.

25. The device according to claim 1, wherein the at least one severance element has an electrically conductive connection with the securing means.

26. The device according to claim 25, wherein the at least one electrolytically corrodible severance element has the conductive connection with the securing means via the at least one stabilization helix.

27. The device according to claim 1, wherein the severance element is in electrical conduction with the securing means and the stabilization helix, the securing means and the stabilization helix being distal to the severance element.

28. The device according to claim 1, wherein the at least one occlusion helix is electrically isolated from the stabilization helix and the securing means.

29. The device according to claim 1, wherein the helical proximal portion of the at least one stabilization helix comprises an insulative coating on an outer surface thereof.

30. The device according to claim 1, wherein the helical proximal portion of the at least one stabilization helix comprises a plurality of helical windings.

* * * * *